(12) United States Patent
Kalmann et al.

(10) Patent No.: US 7,410,494 B2
(45) Date of Patent: Aug. 12, 2008

(54) DEVICE FOR GRASPING AND/OR SEVERING

(75) Inventors: Menno Kalmann, Elspeet (NL); Franciscus Laurens Moll, Bosch en Duin (NL)

(73) Assignee: International and Surgical Innovations, LLC, Campbell Hall, NY (US)

( * ) Notice: Subject to any disclaimer, the term of this patent is extended or adjusted under 35 U.S.C. 154(b) by 404 days.

(21) Appl. No.: 10/870,943

(22) Filed: Jun. 21, 2004

(65) Prior Publication Data

US 2005/0021079 A1    Jan. 27, 2005

(30) Foreign Application Priority Data

Jun. 20, 2003   (IE)   .................. 2003/0460

(51) Int. Cl.
    *A61B 17/28*   (2006.01)
    *A61B 17/32*   (2006.01)

(52) U.S. Cl. .............. 606/205; 606/174; 606/207

(58) Field of Classification Search ............. 606/205, 606/207, 208, 210, 211, 170, 171, 174, 175; 81/305; 30/194, 196–199; 403/53, 56–58, 403/104, 217, 57, 119, 170
    See application file for complete search history.

(56) References Cited

U.S. PATENT DOCUMENTS

| | | | |
|---|---|---|---|
| 2,278,720 A * | 4/1942 | Follet ..................... 285/264 |
| 4,576,408 A * | 3/1986 | Maneki .................... 294/99.2 |
| 4,944,093 A | 7/1990 | Falk | |
| 5,147,373 A | 9/1992 | Ferzli ..................... 606/144 |
| 5,176,702 A * | 1/1993 | Bales et al. .............. 606/208 |
| 5,254,129 A * | 10/1993 | Alexander ................ 606/170 |
| 5,254,130 A * | 10/1993 | Poncet et al. ............. 606/206 |
| 5,275,615 A * | 1/1994 | Rose ..................... 606/208 |
| 5,282,826 A | 2/1994 | Quadri .................... 606/207 |
| 5,312,391 A | 5/1994 | Wilk ..................... 606/1 |
| 5,342,381 A | 8/1994 | Tidemand | |
| 5,456,684 A | 10/1995 | Schmidt et al. | |
| 5,496,317 A | 3/1996 | Goble et al. | |
| 5,573,535 A | 11/1996 | Viklund | |
| 5,613,977 A | 3/1997 | Weber et al. | |
| 5,626,595 A | 5/1997 | Sklar et al. | |
| 5,782,747 A | 7/1998 | Zimmon | |

(Continued)

FOREIGN PATENT DOCUMENTS

DE          3322741 A1     1/1985

(Continued)

*Primary Examiner*—Todd E. Manahan
*Assistant Examiner*—Ryan Severson
(74) *Attorney, Agent, or Firm*—Neil D. Gershon

(57) ABSTRACT

A surgical device (101) for grasping and severing body tissue comprises a housing (140) which defines a proximal end (102) and a distal end (104), a user operating handle (160) at the proximal end (102), and two blade elements (110, 120) at the distal end (104). The user operating handle (160) may be activated to pivot the blade elements (110, 120) about two parallel grasping pivot axes to grasp a piece of body tissue which is located between the blade elements (110, 120). The user operating handle (160) may also be activated to pivot the blade elements (110, 120) about a severing pivot axis to sever a piece of body tissue which is located between the blade elements (110, 120).

52 Claims, 6 Drawing Sheets

U.S. PATENT DOCUMENTS

| | | |
|---|---|---|
| 5,797,936 A | 8/1998 | Kleihues ............... 606/167 |
| 5,893,835 A | 4/1999 | Witt et al. ............... 601/2 |
| 5,908,420 A | 6/1999 | Parins et al. |
| 5,984,938 A | 11/1999 | Yoon |
| 5,984,939 A | 11/1999 | Yoon |
| 6,017,358 A | 1/2000 | Yoon et al. |
| 6,024,744 A | 2/2000 | Kese et al. |
| 6,214,028 B1 | 4/2001 | Yoon et al. |
| 6,358,268 B1 | 3/2002 | Hunt et al. |
| 6,391,043 B1 * | 5/2002 | Moll et al. ............... 606/174 |
| 6,425,896 B1 | 7/2002 | Baltschun et al. |
| 6,506,208 B2 | 1/2003 | Hunt et al. |
| 6,589,231 B1 | 7/2003 | Gobron et al. |
| 6,773,434 B2 | 8/2004 | Ciarrocca |
| 6,814,745 B2 | 11/2004 | Prestel |
| 6,976,992 B2 | 12/2005 | Sachatello et al. |
| 7,087,070 B2 | 8/2006 | Flipo |
| 7,208,005 B2 | 4/2007 | Frecker et al. |
| 2001/0005787 A1 * | 6/2001 | Oz et al. ............... 606/142 |
| 2003/0065358 A1 * | 4/2003 | Frecker et al. ............... 606/205 |

FOREIGN PATENT DOCUMENTS

| | | |
|---|---|---|
| DE | 4400409 A1 | 7/1995 |
| WO | WO94/05224 | 3/1994 |

* cited by examiner

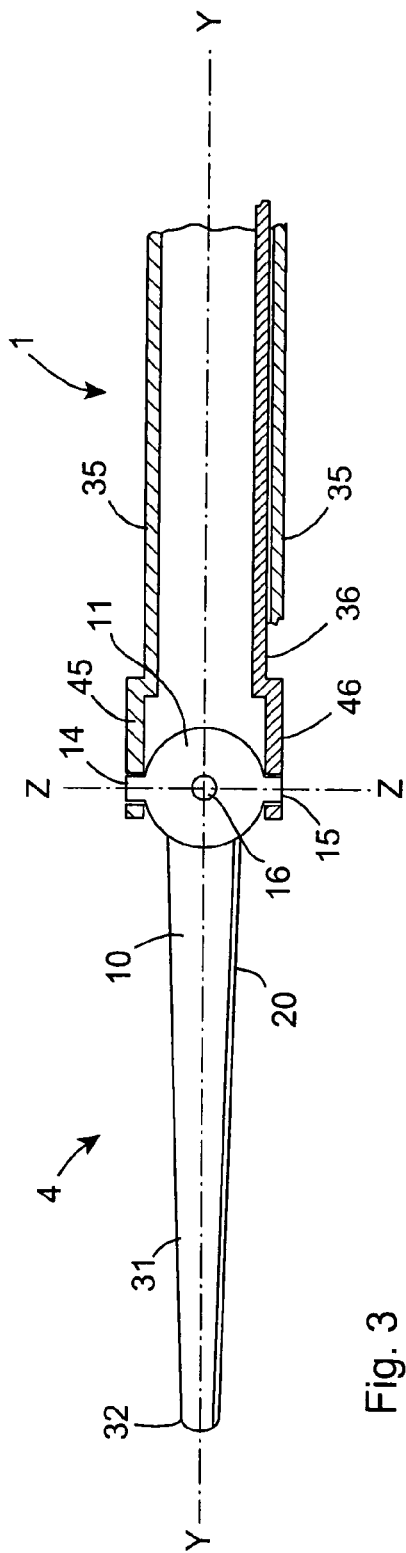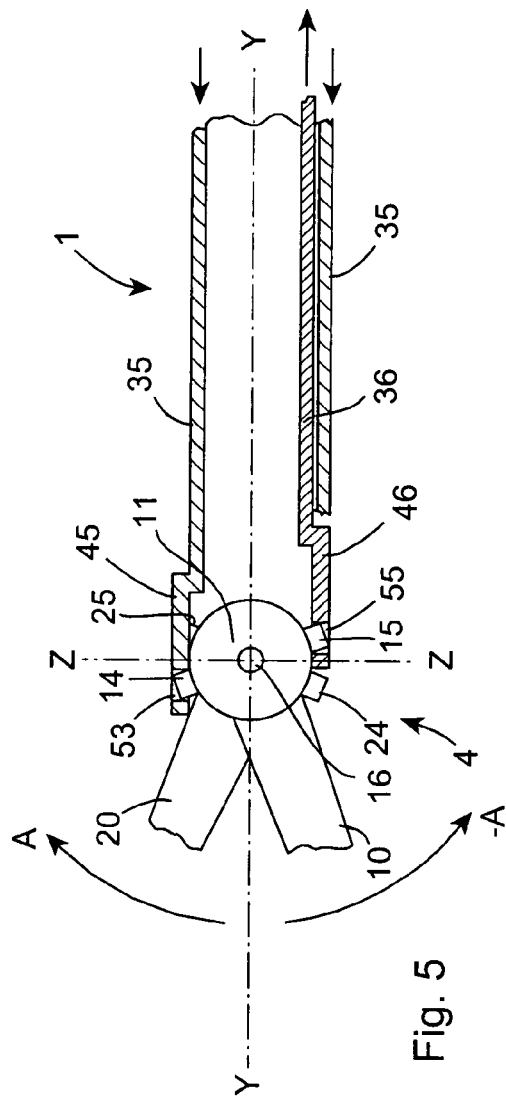
Fig. 3
Fig. 5

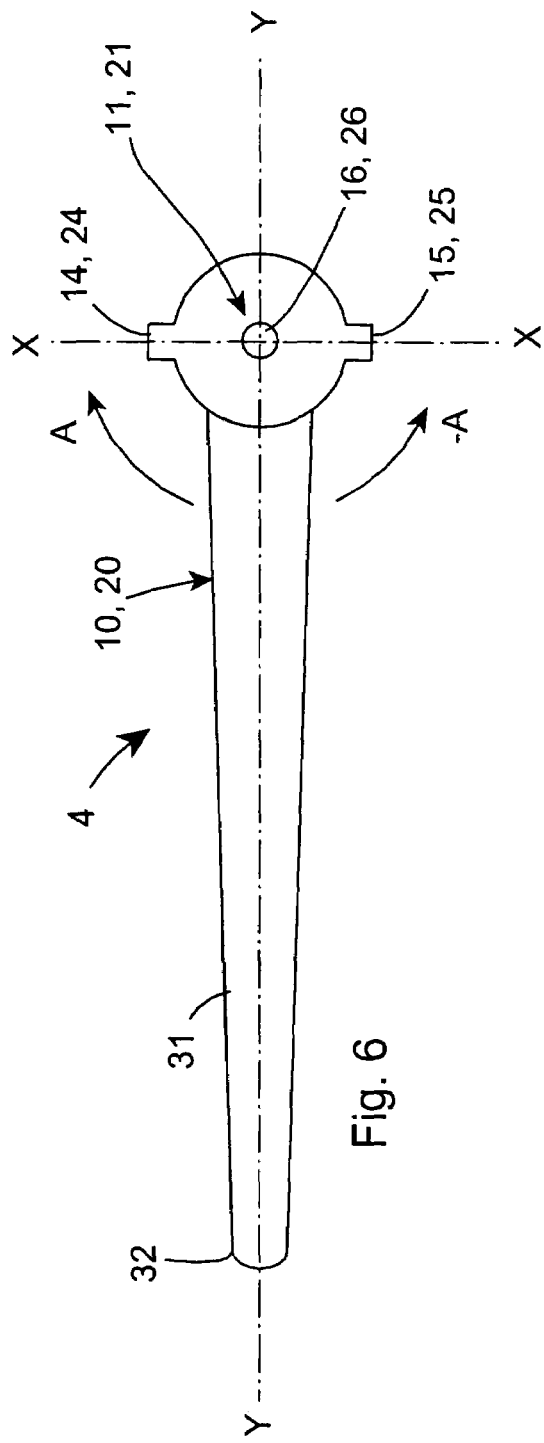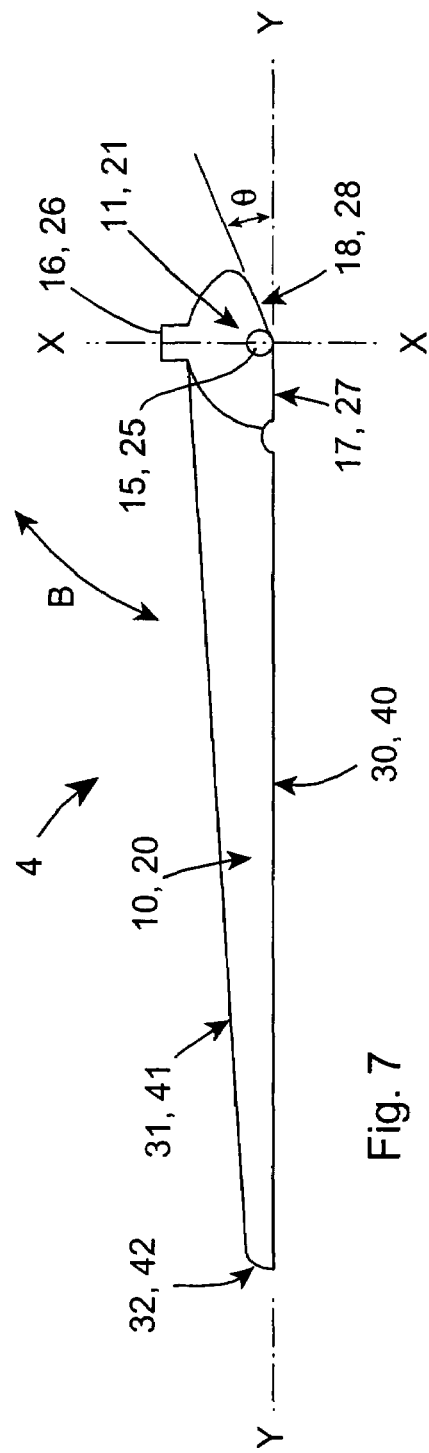

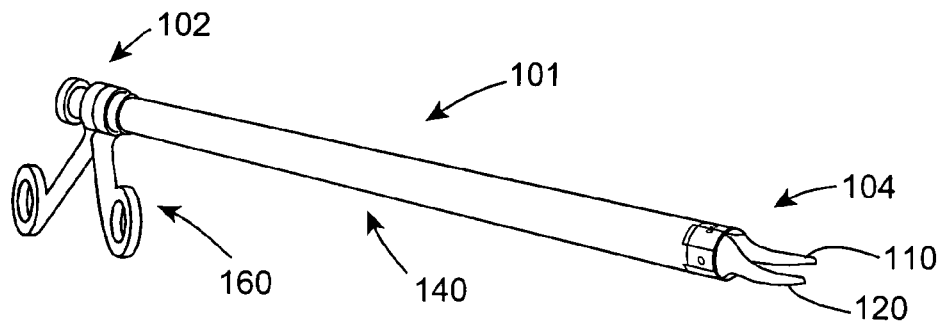
Fig. 9
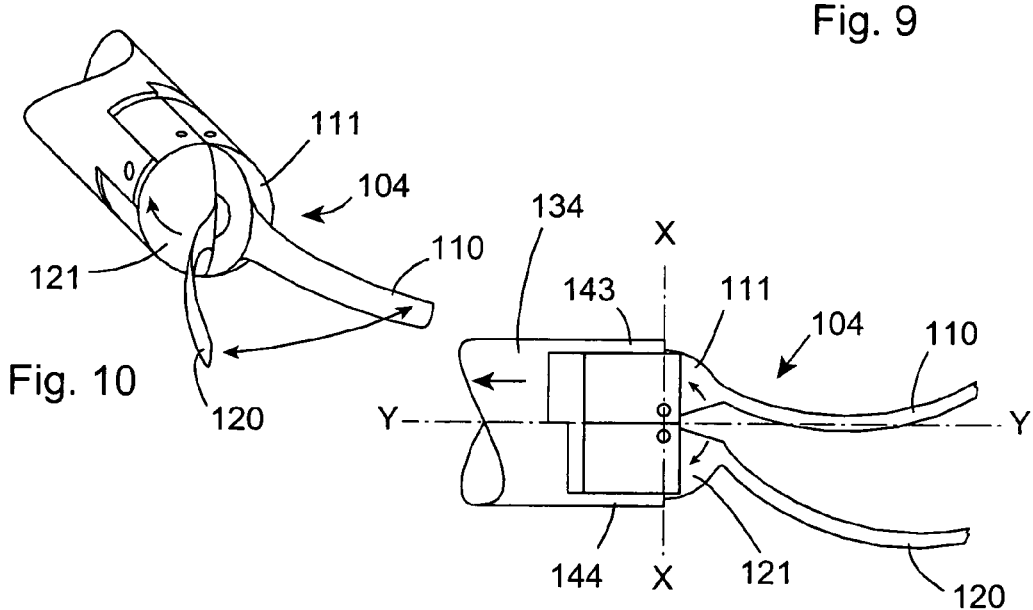
Fig. 10
Fig. 11
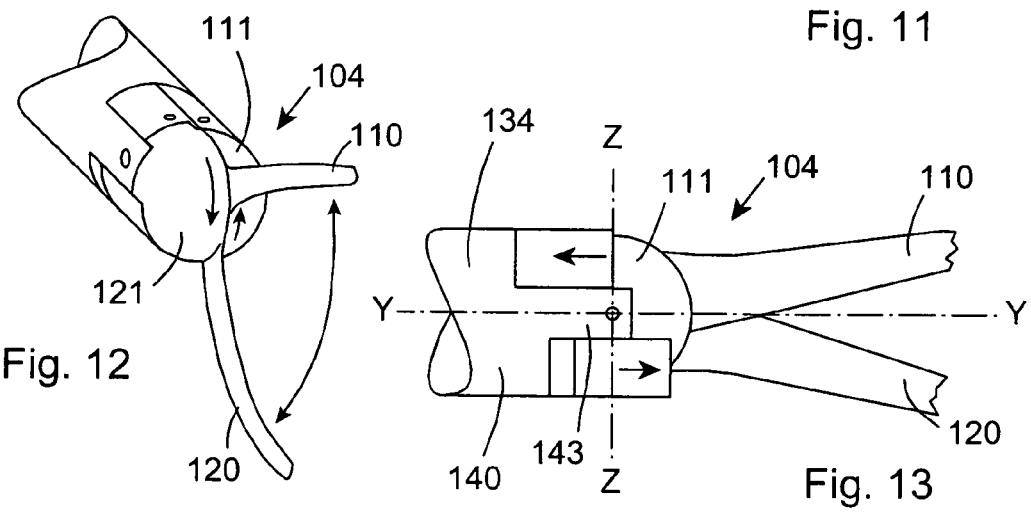
Fig. 12
Fig. 13

DEVICE FOR GRASPING AND/OR SEVERING

This invention relates to a device for grasping and/or severing.

During a surgical procedure when body tissue is to be removed from a body cavity, it is often required that the body tissue be securely held, so that the body tissue can be severed. It is known for a surgeon carrying out such a surgical procedure to use one instrument for grasping and securely holding the body tissue, and to use a second separate instrument to sever the body tissue. However such an approach requires a great deal of skill on the part of the surgeon to operate the two separate instruments simultaneously, often in addition to operating other instruments, such as an endoscope. Furthermore the use of two instruments generally requires a greater working space in the body cavity and a larger incision to accommodate the two different surgical instruments.

In U.S. Pat. No. 6,391,043 a surgical device for use in grasping and severing body tissue is described.

This invention is aimed at providing an improved device for grasping and/or severing.

STATEMENTS OF INVENTION

According to the invention there is provided a device for grasping and/or severing, the device comprising:

a first operative element and a second operative element;

at least one of the operative elements being pivotable about a grasping pivot axis for grasping an object located between the operative elements; and at least one of the operative elements being pivotable about a severing pivot axis for severing an object located between the operative elements;

the grasping pivot axis intersecting the severing pivot axis.

The device of the invention provides a particularly simple mechanism to enable an object, such as a piece of body tissue, to be grasped and to be severed.

By arranging the pivot axes such that the grasping pivot axis intersects the severing pivot axis, the overall size of the device is minimised. This space-saving aspect of the invention may be particularly important when the device is used during a surgical procedure, in which case the working space available within a body cavity to perform the grasping and severing actions may be limited.

In one embodiment of the invention the point of intersection of the grasping pivot axis with the severing pivot axis is in the region of the proximal end of each operative element.

In a preferred case the device comprises a housing defining a proximal end and a distal end, and the first operative element and the second operative element are provided at the distal end of the housing. Ideally the operative element is pivotable relative to the housing about the grasping pivot axis. Most preferably the operative element is pivotable relative to the housing about the severing pivot axis. The first operative element may be pivotable relative to the housing about a first grasping pivot axis, and the first operative element is pivotable relative to the housing about a first severing pivot axis. The second operative element may be pivotable relative to the housing about a second grasping pivot axis, and the second operative element is pivotable relative to the housing about a second severing pivot axis. Preferably the first grasping pivot axis is parallel to the second grasping pivot axis. Ideally the first grasping pivot axis is spaced apart from the second grasping pivot axis. Preferably the first severing pivot axis is parallel to the second severing pivot axis. Ideally the first severing pivot axis is co-axial with the second severing pivot axis.

In another embodiment the device may comprise at least one actuating element for controlling pivoting of the operative element from a proximal end of the device. The actuating elements provide the user with a degree of control from the proximal end of the device over the grasping and severing actions of the operative elements. In this manner the device may be used to grasp and sever in a difficult-to-access location, for example in a body cavity having a narrow access opening. Preferably the actuating element is translatable to control pivoting of the operative element. The device may comprise a first actuating element connected to the operative element for controlling pivoting of the operative element relative to the housing about the grasping pivot axis. Ideally the first actuating element is connected to the first operative element for controlling pivoting of the first operative element relative to the housing about the first grasping pivot axis, and the first actuating element is connected to the second operative element for controlling pivoting of the second operative element relative to the housing about the second grasping pivot axis. The device may comprise a second actuating element connected to the operative element for controlling pivoting of the operative element relative to the housing about the severing pivot axis. Ideally the second actuating element is connected to the first operative element for controlling pivoting of the first operative element relative to the housing about the first severing pivot axis, and the second actuating element is connected to the second operative element for controlling pivoting of the second operative element relative to the housing about the second severing pivot axis. The device may comprise a third actuating element connected to the operative element for controlling pivoting of the operative element relative to the housing about the severing pivot axis. Ideally the third actuating element is connected to the first operative element for controlling pivoting of the first operative element relative to the housing about the first severing pivot axis, and the third actuating element is connected to the second operative element for controlling pivoting of the second operative element relative to the housing about the second severing pivot axis.

In one case one of the operative element or the actuating element comprises at least one male projection configured to be received in at least one corresponding female recess in the other of the actuating element or the operative element to connect the actuating element to the operative element. Preferably the operative element comprises the at least one male projection and the actuating element comprises the at least one corresponding female recess. Ideally the male projection is rotatably received in the corresponding female recess. Most preferably pivot axis extends through the male projection. The co-operating male projection and female recess provide a means of connecting the operative element to the actuating element, and also provide a means by which the operative element may pivot relative to the housing.

The actuating element may comprise a generally cylindrical part extending distally from a proximal end of the housing. Preferably the actuating element comprises one or more arms extending distally from a distal end of the cylindrical part to the distal end of the housing. Ideally the or each actuating element comprises two diametrically opposed arms. Most preferably the actuating element is connected to the operative element at the one or more arms. The one or more arms of the first actuating element and the one or more arms of the second actuating element and the one or more arms of the third actuating element may be configured to facilitate connection of each of the actuating elements to both the first operative element and the second operative element. Preferably the one or more arms of the actuating elements are staggered radially around the circumference of the operative elements. The arms of the cylindrical actuating elements enable all three actuating elements to be connected to both operative elements.

In one embodiment the device comprises two or more actuating elements and the actuating elements extend co-axially. Preferably the first actuating element is located radially outwardly of the second actuating element. Preferably the second actuating element is located radially outwardly of the third actuating element.

The or each actuating element may comprise a user control element at the proximal end of the device. Preferably the user control element comprises a handle.

In a preferred case the housing comprises the first actuating element and the second actuating element and the third actuating element.

The operative element may comprise a support element pivotably connected to the distal end of the housing. Preferably the support element of the first operative element contacts the support element of the second operative element. Ideally the support element of the first operative element contacts the support element of the second operative element along a plane substantially parallel to the grasping pivot axis. Most preferably the first operative element is pivotable relative to the housing about the first grasping pivot axis between a closed configuration and an open configuration for grasping an object:

in the closed configuration, the support element of the first operative element contacting the support element of the second operative element along a first base surface of the support element of the first operative element;

in the open configuration, the support element of the first operative element contacting the support element of the second operative element along a second base surface of the support element of the first operative element.

The plane of the or each base surface may be substantially parallel to the grasping pivot axis. Preferably the angle defined between the first base surface and the second base surface is less than 180 degrees. Ideally the angle defined between the first base surface and the second base surface is greater than 90 degrees. Because the first base surface is arranged at an angle to the second base surface, this enables the support element to pivot between the closed configuration and the open configuration. The support element may comprise the first base surface, the second base surface and a curved surface. In one case the support element is substantially hemi-spherical in shape.

The support element may comprise an apex projection projecting from an apex of the support element, a first side projection projecting from a first side of the support element, and a second side projection projecting from a second side of the support element. Preferably a first side projection and the second side projection protrude in opposite directions from an external surface of the support element.

In a further embodiment the operative element comprises a blade element for grasping and/or severing an object. Preferably the blade element is formed integrally with the support element.

The grasping pivot axis is preferably arranged substantially perpendicular to the severing pivot axis.

The invention also provides in another aspect a device for grasping and/or severing, the device comprising:

a housing defining a proximal end and a distal end; and a first operative element and a second operative element at the distal end of the housing;

at least one of the operative elements being pivotable relative to the housing about a grasping pivot axis for grasping an object located between the operative elements; and at least one of the operative elements being pivotable relative to the housing about a severing pivot axis for severing an object located between the operative elements;

the housing comprising a first actuating element, a second actuating element and a third actuating element;

the first actuating element being connected to the operative element, the severing pivot axis being defined by the connection of the first actuating element to the operative element; and the second actuating element being connected to the operative element and the third actuating element being connected to the operative element, the grasping pivot axis being defined by the connections of the second actuating element and the third actuating element to the operative element.

The connection of the actuating element to the operative element also provides the means by which the operative element may pivot relative to the housing, and in this manner the overall size of the device is minimised.

In one embodiment the actuating element is connected to the operative element by a pivot member. Preferably the operative element comprises a male projecting pivot member configured to be received in a corresponding female recess in the actuating element. Ideally the pivot axis extends through the pivot member.

In a further aspect the invention provides a device for grasping and/or severing, the device comprising:

a housing defining a proximal end and a distal end; and a first operative element and a second operative element at the distal end of the housing;

each operative element comprising a support block connected to the housing, and an elongate blade element extending distally from the support block;

at least one of the blade elements being movable relative to the housing in a grasping action to grasp an object located between the operative elements; and at least one of the blade elements being movable relative to the housing in a severing action to sever an object located between the operative elements.

The device according to the invention has been found to provide the user with enhanced control over the motion of the operative elements. In particular the positions of the operative elements may be more precisely controlled during both the severing action and the grasping action to enable the user to achieve a more effective severing or grasping.

In one case the support block of the first operative element contacts the support block of the second operative element.

The housing may define an inner lumen, and the two support blocks may be at least partially located within the inner lumen in a snug fit. Preferably the two support blocks together have a combined cross-sectional area substantially equal to the cross sectional area of the inner lumen.

In one case the support block is substantially hemi-spherical in shape.

The surgical device of the invention may be employed for grasping and/or severing an object during a surgical procedure.

The invention provides in a further aspect a surgical device comprising a first distal blade element and a second distal blade element for severing and/or grasping, and a proximal user operating part;

wherein the first blade element and the second blade element are movable relative to each other in a first direction in a grasping action, and in a second direction in a severing action;

wherein the first blade element extends from a first support element, and the second blade element extends from a second support element; and wherein the support elements are movably coupled, and axes, about which said support elements are movable, intersect substantially at a centroid of a coupling defined by the support elements.

In yet another aspect of the invention, there is provided a surgical device comprising first and second distal operable elements and a proximal user operating part, wherein the operable elements extend from first and second support elements;

wherein the operable elements are movable relative to each other in a plurality of directions; and wherein the support elements are movably coupled, and axes, about which the support elements are movable, intersect substantially at a centroid of a coupling defined by the support elements.

The invention also provides in another aspect a coupling comprising first and second support elements, which are movable relative to one another in a first direction in a grasping action and in a second direction in a severing action, and axes, about which the support elements are movable, intersect substantially at a centroid of the coupling.

The coupling may be generally spherical. Preferably each support element is generally hemispherical.

In another aspect of the invention, there is provided a method of grasping and/or severing, the method comprising the steps of:

providing a first operative element and a second operative element;

providing a first actuating element, a second actuating element and a third actuating element;

moving the first actuating element relative to the second actuating element and the third actuating element to pivot at least one of the operative elements to grasp an object located between the operative elements; and moving the second actuating element relative to the first actuating element in a first direction and moving the third actuating element relative to the first actuating element in a second direction opposite to the first direction to pivot at least one of the operative elements to sever an object located between the operative elements.

Preferably moving the first actuating element relative to the second actuating element and the third actuating element pivots the first operative element and the second operative element in opposite directions to grasp an object located between the operative elements.

Desirably moving the second actuating element relative to the first actuating element in the first direction and moving the third actuating element relative to the first actuating element in the second direction pivots the first operative element and the second operative element in opposite directions to sever an object located between the operative elements.

The actuating element may be moved by translating the actuating element.

The surgical method of the invention may be employed for grasping and/or severing an object during a surgical procedure.

BRIEF DESCRIPTION OF THE DRAWINGS

The invention will be more clearly understood from the following description of some embodiments thereof, given by way of example only, with reference to the accompanying drawings, in which:

FIG. 3 is a partially cross-sectional, plan view from above of the distal end of the device of FIG. 1 in the closed configuration;

FIG. 5 is a partially cross-sectional, plan view from above of the distal end of the device of FIG. 1 in an open severing configuration;

FIG. 6 is a plan view from above of an operative element of the device of FIG. 1;

FIG. 7 is a side view of the operative element of FIG. 6;

FIG. 9 is a perspective view of another device for grasping and/or severing according to the invention;

FIG. 10 is an enlarged, perspective view of a distal end of the device of FIG. 9 in an open grasping configuration;

FIG. 11 is a plan view from above of the distal end of the device of FIG. 9 in the open grasping configuration;

FIG. 12 is an enlarged, perspective view of the distal end of the device of FIG. 9 in an open severing configuration; and FIG. 13 is a side view of the distal end of the device of FIG. 9 in the open severing configuration.

DETAILED DESCRIPTION

Figure 1:
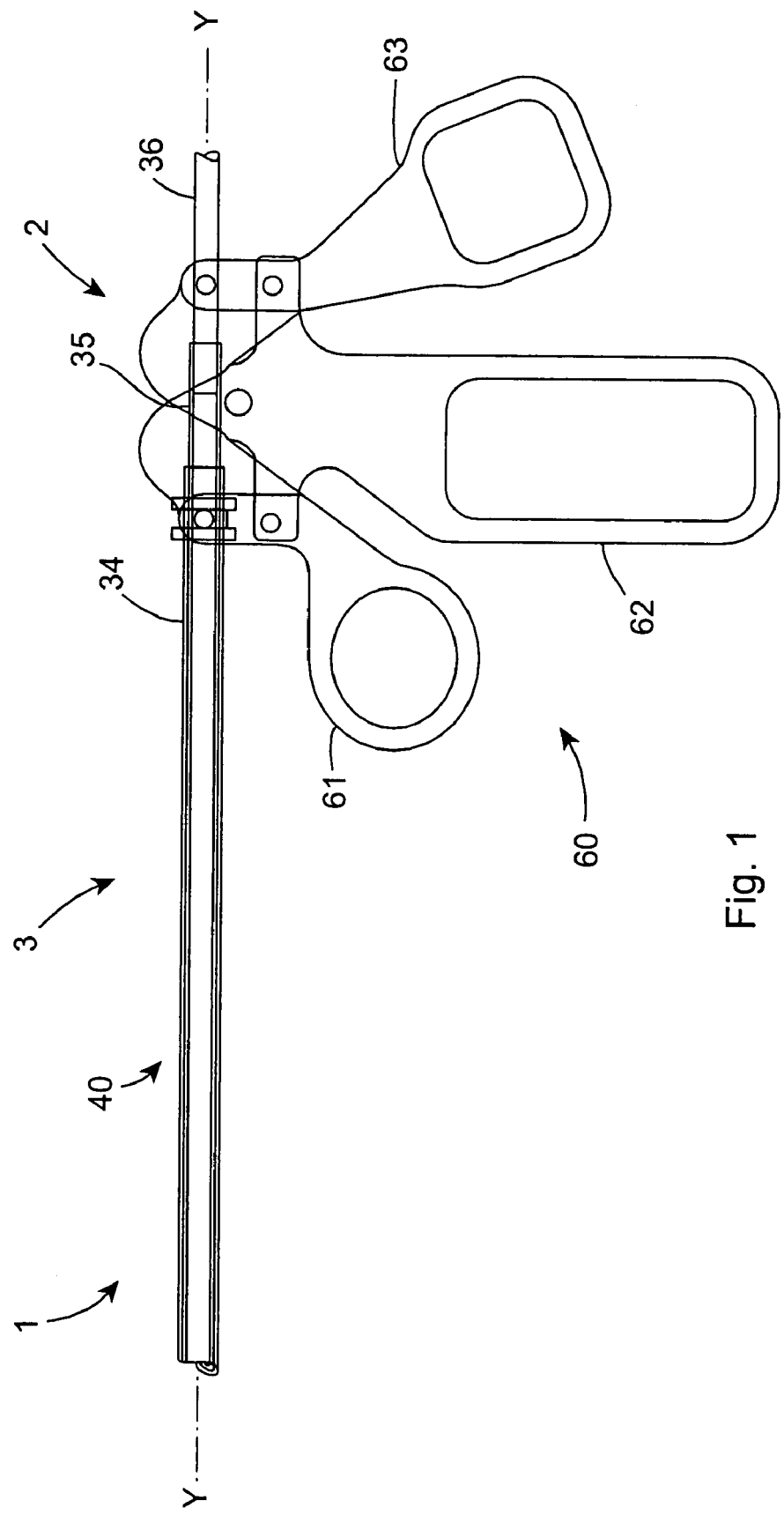
FIG. 1 is a side view of a proximal end of a device for grasping and/or severing according to the invention.
Figure 2:
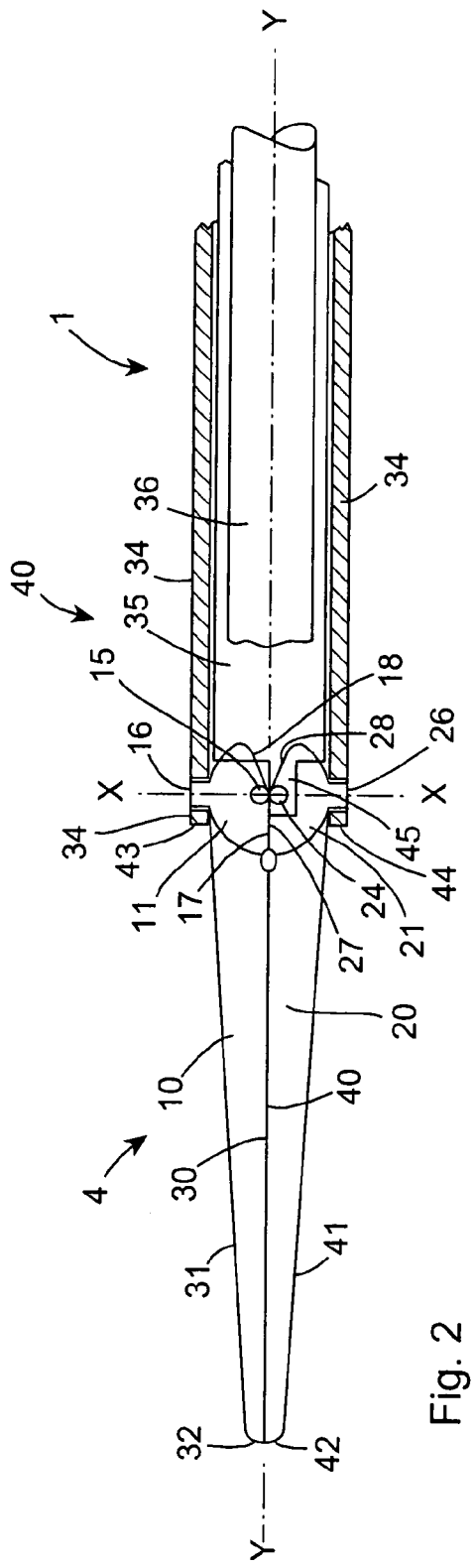
FIG. 2 is a partially cross-sectional, side view of a distal end of the device of FIG. 1 in a closed configuration.

Referring to the drawings, in particular FIGS. 1, 2 and 3, the device 1 comprises a proximal end 2, an intermediate portion 3, and a distal end 4. A first blade element 10 and a second blade 20 extend from the intermediate portion of the device 1 at the distal end 4. User operating means 60 are provided near the proximal end 2. The intermediate portion 3 of the device comprises an actuating means and a housing 40.

Referring to FIGS. 1, 2, 6, 7 and 8, the blade elements 10, 20 are elongated and comprise distal tips 32, 42, cutting edges 30, 40, and backs 31, 41 respectively. The blade elements 10, 20 extend from block-shaped support elements 11, 21 respectively.

While the blade elements 10, 20 and the support elements 11, 21 are substantially similar, for purposes of clarity, similar features of the elements have been indicated by different numerals respectively in the drawings and description.

Figure 4:
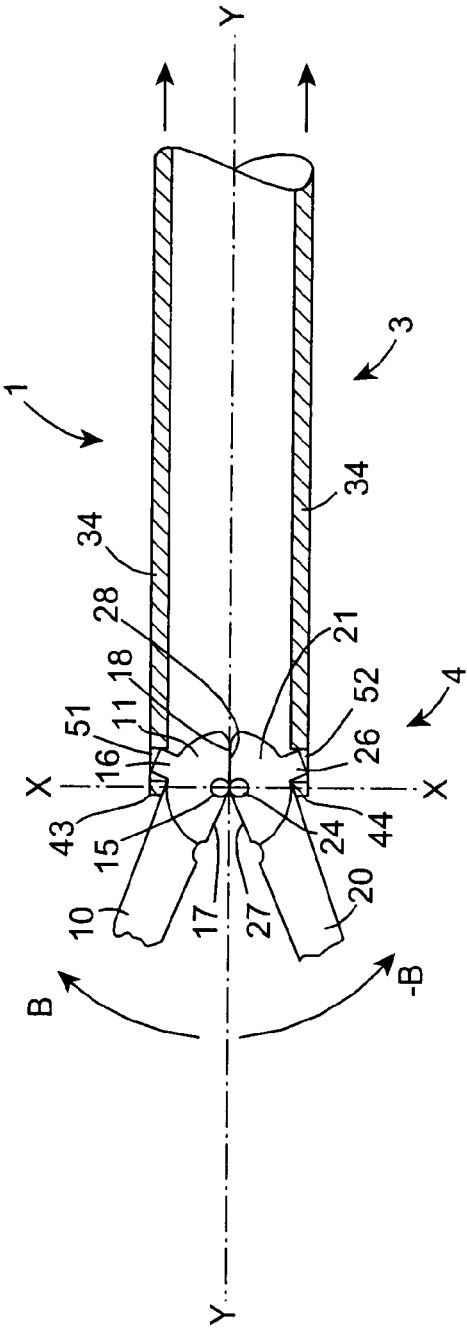
FIG. 4 is a partially cross-sectional, side view of the distal end of the device of FIG. 1 in an open grasping configuration.

The support elements 11, 21 are generally hemispherical in form and comprise external curved surfaces 13, 23 and substantially flat faces 12, 22 respectively. The support elements 11, 21 are partially cut-away, with a second planar base portion 18, 28 of each face being arranged at an angle θ to a first planar base portion 17, 27 thereof (FIG. 7). The angle θ is less than 180° to enable pivoting of the support elements 11, 21 to an open grasping configuration (FIG. 4). The planar base portions 18, 28, 17, 27 are arranged parallel to the Z-axis.

The support elements 11, 21 are mounted in the device housing 40 so that the element 21 which supports the blade element 20 is inverted relative to the element 11 which supports the blade element 10.

The support elements 11, 21 are mounted near the distal end of the housing 40 partially within the housing 40 in a snug fit. The blade elements 10, 20 are formed integrally with the front curved portions of the support elements 11, 21 and extend therefrom in the distal direction. The support elements 11, 21 which are contained within the housing 40 are distinct and independent of one another, and are not inter-linked or connected to one another. When mounted in the housing 40 they are held in proximity to each other substantially about a centroid. The coupling defined by the support elements 11, 21 is generally spherical in form (FIG. 2). The faces 12, 22 of the two coupled elements 11, 21 are aligned.

In the closed configuration, the blade elements 10, 20 of the device 1 substantially abut each other (FIG. 2). The support elements 11, 21 are also substantially abutting with the first planar portions 17, 27 being held in contact (FIG. 2).

As illustrated, and for the purposes of this description, the Y-axis of the device 1 is defined as running from the proximal end 2 to the distal end 4, and is the longitudinal axis of the device 1. The X-axis is taken as running through a centroid of the coupling defined by the support elements 11, 21 at right angles to the Y-axis (FIG. 2).

The blade elements 10, 20 and support elements 11, 21 are movable about two distinct axes. Firstly, they are movable about the X-axis in the directions A, −A (FIG. 5). Secondly, since the faces 12 and 22 of the support elements 11, 21 are partially cut-away, the support elements 11, 21 may be tilted or rotated with respect to each other in directions B, −B about axes parallel to the Z-axis (FIG. 4). Thus the support elements 11, 21 and the attached blade elements 10, 20 are movable about two different axes. The axes about which they are movable intersect substantially at a centroid of the coupled support elements 11, 21.

The coupling defined by the support elements 11, 21 and the associated housing 40 comprise means to facilitate controlled movement of the support elements 11, 21 relative to the housing 40. In effect, the actuating means for moving the blade elements 10, 20 comprises the support elements 11, 21 arranged to interact with the housing 40. The housing 40 comprises three movable sleeves 34, 35, 36, which are connected to the user operating means 60. The sleeves 34, 35, 36 act as actuating elements to enable a user to control the pivoting of the blade elements 10, 20 relative to the housing 40 from the proximal end 2.

Figure 8:
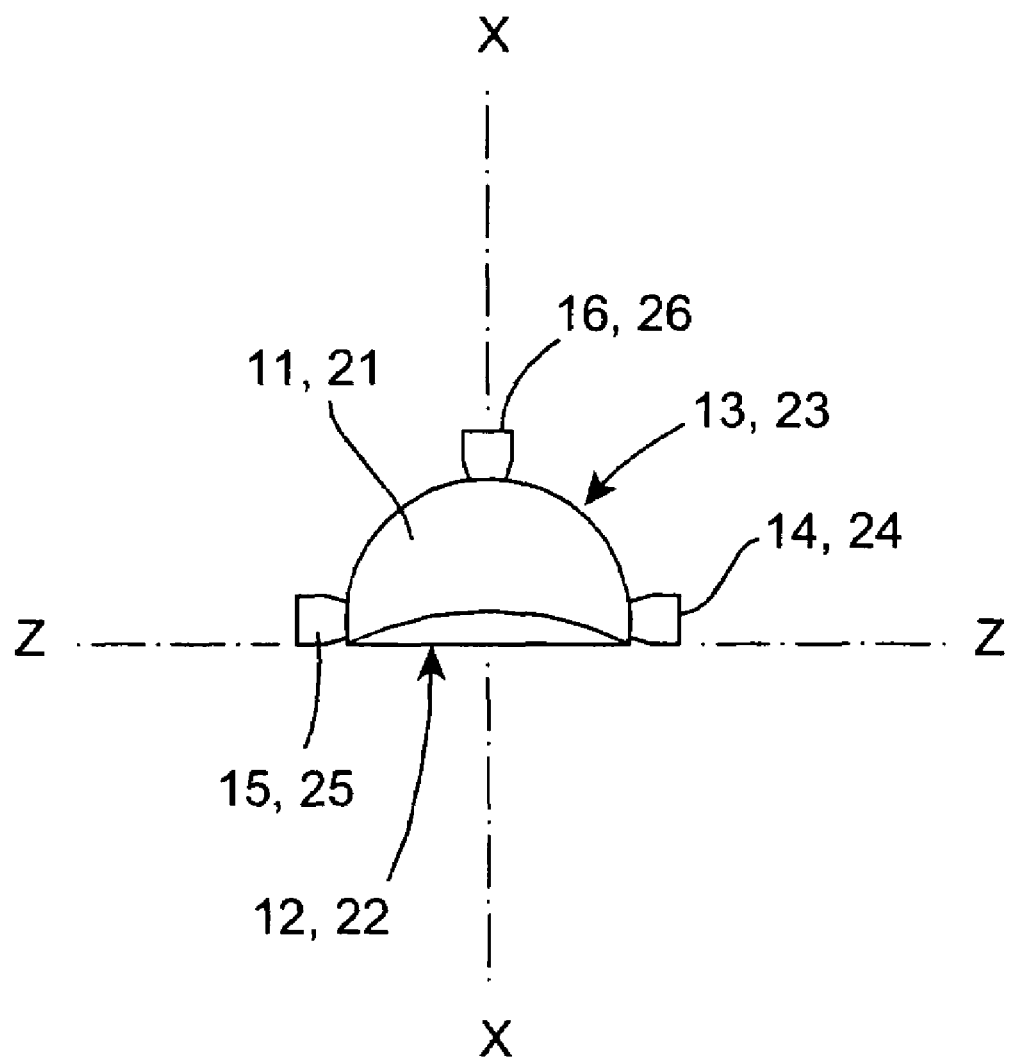
FIG. 8 is an end view of the operative element of FIG. 6.

Referring to FIGS. 6, 7 and 8, the support elements 11, 21 comprise a series of pins protruding from the curved external surfaces 13, 23 thereof. The support element 11 comprises side pins 14 and 15 and a top pin 16 protruding from the top surface thereof. Similarly the support element 21 comprises side pins 24 and 25 and a top pin 26.

Referring to FIGS. 2, 3, 4 and 5, the pins co-operate with recesses or slots on the internal surfaces of the sleeves 34, 35, 36. The housing 40 comprises an outer sleeve 34, an intermediate sleeve 35 and an inner sleeve 36. The outer sleeve 34 has a radius sufficient to accommodate the other sleeves 35, 36 and the support elements 11, 21. As illustrated in FIG. 2 when the device 1 is in the closed configuration, the outer sleeve 34 extends beyond the top pins 16, 26 and the centroid of the coupled support elements 11, 21 towards the distal end 4 of the device 1. The sleeves 34, 35, 36 are substantially cylindrical in form and arranged in a co-axial manner with the intermediate sleeve 35 located within the outer sleeve 34, and with the inner sleeve 36 located within the intermediate sleeve 35.

Referring to FIGS. 2, 3, 4 and 5, the sleeves 34, 35, 36 each comprise arms which extend to the protruding pins of the support elements 11, 21. With the device 1 in the closed configuration (as illustrated in FIGS. 2 and 3) the ends of the arms of the sleeves are in alignment. In the closed configuration, the distal end 4 of housing 40 has a cylindrical form and surrounds the support elements 11, 21. The cylindrical form is comprised of the six separate arms extending from the sleeves 34, 35, 36. The sleeve 34 comprises arms 43, 44, the sleeve 35 comprises arms 45, 47 and the sleeve 36 comprises arms 46, 48. The arms are of equal width and are curved in shape. The arms are radially staggered around the circumference of the housing 40 so that when aligned in the closed configuration together the arms form a continuation of the cylindrical form of the outer sleeve 34 which extends to the support elements 11, 21. The arms 43, 44 are a continuation of the sleeve 34. The arms 45, 47 are necessarily arranged at an angle to the intermediate sleeve 35 for purposes of alignment with the outer sleeve 34 and the arms 43, 44 of the outer sleeve 43. The arms of each individual sleeve are located on opposite sides of the sleeve. Recessed slots for receiving the protruding pins are provided on the internal surfaces of the arms of the sleeves.

The external sleeve 34 comprises recessed slots 51, 52 for receiving top pins 16, 26 respectively. Similarly, the intermediate sleeve 35 comprises recessed slots (not shown) for receiving pins 14, 24 respectively, and the inner sleeve 36 comprises recessed slots (not shown) for receiving pins 15, 25. When the device 1 is assembled for use the pins 14, 24 are on opposite sides of the device 1 respectively as are the pins 15, 25.

The sleeves 34, 36 are movable in the distal and proximal directions by translation.

User operating means 60 are provided near the proximal end 2 of the device 1. The actuating means of the device 1 comprises the sleeves 34, 35, 36, which are moved in response to user operation of the operating means 60 to affect pivoting of the support elements 11, 21.

Movement of the support elements 11, 21 results in the movement of the integral blade elements 10, 20 in a severing or a grasping action. The effect of movement of the sleeves 34, 35, 36 is to exert forces on the support elements 11, 21 by means of the pins co-operating with the recesses on the internal surfaces of the sleeves 34, 35, 36. Depending on the required action i.e. a severing or grasping action, the relative positions of the components of the device 1 and their movement relative to each other is as follows:

Device at Rest: (FIGS. 2 and 3)

The blade elements 10, 20 are closed and substantially abut each other. The first face portions 17, 27 of the support elements 11, 21 are also substantially abutting and their perimeter edges are aligned. The sleeves 34, 35 and 36 are in the rest configuration.

Grasping Action (FIGS. 2 and 4):

The outer sleeve 34 is moved towards the proximal end 2 of the device 1 relative to the sleeves 35, 36, which remain stationary. This has the effect of exerting forces on the top pins 16, 26 in the proximal direction to pivot the support elements 11, 21 about grasping pivot axes which are parallel to Z-axis of the device 1 so that the blade elements 10, 20 are separated in the direction B, −B. The support element 11 turns in the direction B pivoting about the pins 14, 15 and the support element 21 turns in the direction −B pivoting about the pins 24, 25.

The grasping pivot axis for the support element 11 is provided by an axis which extends through the two pins 14, 15, and the grasping pivot axis for the support element 21 is provided by an axis which extends through the two pins 24, 25. These two pivot axes are parallel, and are spaced-apart by the distance between the side pins 14, 15 of one support element 11 and the side pins 24, 25 of the other support element 21.

The device 1 is thus opened to the open grasping configuration. Movement of the sleeve 34 in the opposite direction results in the blade elements 10, 20 being closed in a grasping action.

Severing Action (FIGS. 3 and 5):

The inner sleeve 36 is moved relative to the intermediate sleeve 35, and the outer sleeve 34 is held stationary. In the illustrated embodiment, the inner sleeve 36 is moved proximally and the intermediate sleeve 35 is moved distally. This has the effect of exerting a force on the side pin 14 in the distal direction and a force on the side pin 15 in the proximal direction to pivot the support element 11 in the direction −A, and has the effect of exerting a force on the side pin 24 in the distal direction and a force on the side pin 25 in the proximal direction to pivot the support element 21 in the direction A in the Y-Z plane of the device 1 pivoting about the X-axis, which acts as the severing pivot axis for both support elements 11, 21.

The support element 11 turns in the direction −A pivoting about the pin 16, and the support element 21 turns in the direction A pivoting about the pin 26. The device 1 is thus opened to the open severing configuration.

Movement of the inner sleeve 36 distally and the intermediate sleeve 35 proximally results in the blades 10, 20 being closed in a severing configuration.

The severing pivot axis through the X-axis is perpendicular, in this case, to the grasping pivot axes which are parallel to the Z-axis.

Referring to FIG. 1, the user operating means 60 comprises handles 61, 63 and a central support 62. The central support 62 is attached to the intermediate sleeve 35, the handle 61 is attached to the outer sleeve 34 and the handle 63 is attached to the inner sleeve 36. A user operates the device 1 by means of operating the user operating means 60 to cause movement of the sleeves 34, 35, 36 as required. In the grasping action, the handle 61 is operated to move the outer sleeve 34 relative to the other two sleeves 35, 36. In the severing action, the handle 63 and the central support 62 are operated to move the inner sleeve 36 and the intermediate sleeve 35.

While in the present embodiment a user operating means 60 comprising handles is used to selectively actuate the actuating means, it will be appreciated that any other suitable arrangement may also be used.

Referring to FIGS. 9 to 13 a surgical device 101 according to an alternative embodiment of the invention comprises a distal end 104, a proximal end 102, and a housing 140. First and second blade elements 110, 120 extend from the housing 140 at the distal end 104 of the device 101. User operating means 160 are provided near the proximal end 102. As described previously in relation to the first embodiment, the blade elements 110, 120 extend from a coupling defined by support elements 111, 121. The blade elements 110, 120 and support elements 111, 121 are movable in two directions in a grasping action and a severing action. The housing 140 comprises an outer sleeve 134 comprising arms 143, 144 which extend to the support elements 111, 121. The arms 143, 144 of the outer sleeve 134 comprise recessed slots for receiving pins protruding from the apexes of the support elements 111, 121.

The invention provides a surgical device with the advantage that it may be used for both grasping and severing tissue. The actuating means and support means for the blades are substantially enclosed within the body of the apparatus. The grasping and severing actions are achieved by a actuating mechanism which provides for movement about two different axes. It is not necessary to provide separate actuating means to achieve each distinct movement.

Furthermore the severing pivot axis and the grasping pivot axis, about which each support element moves intersect each other. As a result the device is compact.

Furthermore since the actuating means are contained substantially within or integral with the housing of the device, the device does not present any protruding parts which may move to interfere with the surgical procedure at hand.

It will be appreciated that the form of the blade elements is not limited to those illustrated For example, curved blade elements or blade elements of any other suitable form could also be used.

The coupling of the invention may also be used in other suitable applications, for example in gardening tools, shelving support systems and the like.

Operable elements other than blade elements may be provided extending from the support elements. The operable elements may be corresponding elements which co-operate to perform a particular action. Operable elements for any application may be provided for example surgical devices, gardening tools, shelving support systems and the like.

While in the present embodiment the actuating means comprises sleeves substantially of cylindrical form it will be appreciated that any other suitable means may also be used.

The invention is not limited to the embodiments hereinbefore described, with reference to the accompanying drawings, which may be varied in construction and detail.

The invention claimed is:

1. A surgical device for grasping and/or severing, the device comprising:
   a first operative element and a second operative element, each of the operative elements having a cutting edge;
   at least the first operative element being pivotable in a first direction with respect to the second operative element about a grasping pivot axis for grasping an object located between the operative elements; and
   at least the first operative element being pivotable in a second different direction with respect to the second operative element about a severing pivot axis for severing an object located between the operative elements;
   the grasping pivot axis intersecting the severing pivot axis; and
   at least one actuating element for controlling pivoting of the first operative element from a proximal end of the device.

2. A device as claimed in claim 1 wherein the point of intersection of the grasping pivot axis with the severing pivot axis is in the region of the proximal end of each operative element.

3. A device as claimed in claim 1 wherein the device comprises a housing defining a proximal end and a distal end and a longitudinal axis, and the first operative element and the second operative element are provided at the distal end of the housing.

4. A device as claimed in claim 3, wherein the operative element is pivotable relative to the housing about the grasping pivot axis, the grasping pivot axis being transverse to the longitudinal axis of the housing.

5. A device as claimed in claim 3 wherein the operative element is pivotable relative to the housing about the severing pivot axis, the severing axis being transverse to the longitudinal axis of the housing.

6. A device as claimed in claim 3 wherein the first operative element is pivotable relative to the housing about a first grasping pivot axis, and the first operative element is pivotable relative to the housing about a first severing pivot axis.

7. A device as claimed in claim 6 wherein the second operative element is pivotable relative to the housing about a second grasping pivot axis, and the second operative element is pivotable relative to the housing about a second severing pivot axis.

8. A device as claimed in claim 7 wherein the first grasping pivot axis is parallel to the second grasping pivot axis.

9. A device as claimed in claim 7 wherein the first grasping pivot axis is spaced apart from the second grasping pivot axis.

10. A device as claimed in claim 7 wherein the first severing pivot axis is parallel to the second severing pivot axis.

11. A device as claimed in claim 7 wherein the first severing pivot axis is co-axial with the second severing pivot axis.

12. A device as claimed in claim 3 wherein the first operative element comprises a support element pivotably connected to the distal end of the housing.

13. A device as claimed in claim 12 wherein the support element of the first operative element is substantially hemispherical in shape.

14. A device as claimed in claim 1 wherein the first operative element is formed integrally with a support element.

15. A device as claimed in claim 1 wherein the grasping pivot axis is arranged substantially perpendicular to the severing pivot axis, the first operative element moving in the second direction such that it moves in a plane parallel to a plane containing the second operative element.

16. A device as claimed in claim 1 wherein the at least one actuating element is translatable to control pivoting of the first operative element.

17. A device as claimed in claim 1 wherein the device comprises a first actuating element connected to the first operative element for controlling pivoting of the first operative element relative to the housing about the grasping pivot axis.

18. A device as claimed in claim 17 wherein the first actuating element is connected to the first operative element for controlling pivoting of the first operative element relative to the housing about the first grasping pivot axis, and the first actuating element is connected to the second operative element for controlling pivoting of the second operative element relative to the housing about the second grasping pivot axis.

19. A device as claimed in claim 1 wherein the device comprises a second actuating element connected to the operative element for controlling pivoting of the second operative element relative to the housing about the severing pivot axis, the first and second actuating elements being slidable in a longitudinal direction to effect pivoting of the first and second operative elements.

20. A device as claimed in claim 19 wherein the second actuating element is connected to the first operative element for controlling pivoting of the first operative element relative to the housing about the first severing pivot axis, and the second actuating element is connected to the second operative element for controlling pivoting of the second operative element relative to the housing about the second severing pivot axis.

21. A device as claimed, in claim 1 wherein the device comprises a third actuating element connected to the operative element for controlling pivoting of the operative element relative to the housing about the severing pivot axis.

22. A device as claimed in claim 21 wherein the third actuating element is connected to the first operative element for controlling pivoting of the first operative element relative to the housing about the first severing pivot axis, and the third actuating element is connected to the second operative element for controlling pivoting of the second operative element relative to the housing about the second severing pivot axis.

23. A device as claimed in claim 1 wherein one of the first and second operative elements or the actuating element comprises at least one male projection configured to be received in at least one corresponding female recess in the other of the actuating element or the operative element to connect the actuating element to the operative element.

24. A device as claimed in claim 23 wherein one of the first and second operative elements comprises the at least one male projection and the actuating element comprises the at least one corresponding female recess.

25. A device as claimed in claim 23 wherein the male projection is rotatably received in the corresponding female recess.

26. A device as claimed in claim 25 wherein the pivot axis extends through the male projection.

27. A device as claimed in claim 1 wherein the actuating element comprises a generally cylindrical part extending distally from a proximal end of the housing.

28. A device as claimed in claim 27 wherein the actuating element comprises one or more arms extending distally from a distal end of the cylindrical part to the distal end of the housing.

29. A device as claimed in claim 28 wherein the or each actuating element comprises two diametrically opposed arms.

30. A device as claimed in claim 28 wherein the actuating element is connected to the first operative element at the one or more arms.

31. A device as claimed in claim 28 wherein the at least one actuating element comprises first, and second and third actuating elements, and the one or more arms of the first actuating element and the one or more arms of the second actuating element and the one or more arms of the third actuating element are configured to facilitate connection of each of the actuating elements to both the first operative element and the second operative element.

32. A device as claimed in claim 31 wherein the one or more arms of the actuating elements are staggered radially around the circumference of the operative elements.

33. A device as claimed in claim 1 wherein the device comprises two or more actuating elements and the actuating elements extend co-axially and are slidable in a longitudinal direction to effect pivoting of the first actuating element.

34. A device as claimed in claim 33 wherein the first actuating element is located radially outwardly of the second actuating element.

35. A device as claimed in claim 33 wherein the device comprises a third actuating element and the second actuating element is located radially outwardly of the third actuating element.

36. A device as claimed in claim 1 wherein the or each actuating element comprises a user control element at the proximal end of the device.

37. A device as claimed in claim 36 wherein the user control element comprises a handle.

38. A device as claimed in claim 1 further comprising a first actuating element and a second actuating element and a third actuating element.

39. A surgical device for grasping and/or severing, the device comprising:
  a first operative element and a second operative element, each of the operative elements having a cutting edge;
  at least the first operative element being pivotable in a first direction with respect to the second operative element about a grasping pivot axis for grasping an object located between the operative elements; and
  at least the first operative element being pivotable in a second different direction with respect to the second operative element about a severing pivot axis for severing an object located between the operative elements;
the grasping pivot axis intersecting the severing pivot axis;
a housing defining a proximal end and a distal end and a longitudinal axis, and the first operative element and the second operative element are provided at the distal end of the housing, the first operative element comprising a support element pivotably connected to the distal end of the housing;
wherein the support element of the first operative element contacts a support element of the second operative element.

40. A device as claimed in claim 39 wherein the support element of the first operative element contacts the support element of the second operative element along a plane substantially parallel to the grasping pivot axis.

41. A device as claimed in claim 39 wherein the first operative element is pivotable relative to the housing about the first grasping pivot axis between a closed configuration and an open configuration for grasping an object:
in the closed configuration, the support element of the first operative element contacting the support element of the second operative element along a first base surface of the support element of the first operative element;
in the open configuration, the support element of the first operative element contacting the support element of the second operative element along a second base surface of the support element of the first operative element.

42. A device as claimed in claim 41 wherein the plane of the or each base surface is substantially parallel to the grasping pivot axis.

43. A device as claimed in claim 41 wherein the angle defined between the first base surface and the second base surface is less than 180 degrees.

44. A device as claimed in claim 41 wherein the angle defined between the first base surface and the second base surface is greater than 90 degrees.

45. A device as claimed in claim 41 wherein the support element of the first operative element comprises the first base surface, the second base surface and a curved surface.

46. A surgical device for grasping and/or severing, the device comprising:
a first operative element and a second operative element, each of the operative elements having a cutting edge;
at least the first operative element being pivotable in a first direction with respect to the second operative element about a grasping pivot axis for grasping an object located between the operative elements; and
at least the first operative element being pivotable in a second different direction with respect to the second operative element about a severing pivot axis for severing an object located between the operative elements;
the grasping pivot axis intersecting the severing pivot axis;
a housing defining a proximal end and a distal end and a longitudinal axis, and the first operative element and the second operative element are provided at the distal end of the housing, the first operative element comprising a support element pivotably connected to the distal end of the housing;
wherein the support element of the first operative element comprises an apex projection projecting from an apex of the support element of the first operative element, a first side projection projecting from a first side of the support element of the first operative element, and a second side projection projecting from a second side of the support element of the first operative element.

47. A device as claimed in claim 46 wherein the first side projection and the second side projection protrude in opposite directions from an external surface of the support element of the first operative element.

48. A device for grasping and/or severing, the device comprising:
a housing defining a proximal end and a distal end; and
a first operative element and a second operative element at the distal end of the housing;
each operative element comprising a support block having a first pin extending laterally therefrom in a first direction along a first axis and a second pin extending laterally therefrom in a second direction along a second different axis and connected to the housing, and an elongate blade element extending distally from the support block;
at least one of the blade elements being movable relative to the housing in a grasping action along a grasping axis to grasp an object located between the operative elements; and
at least one of the blade elements being movable relative to the housing in a severing action along a severing axis intersecting the grasping axis to sever an object located between the operative elements;
wherein at least one of the support blocks of the operative elements is movable between a first position and a second position to effect the grasping and severing action.

49. A device as claimed in claim 48 wherein the support block of the first operative element contacts the support block of the second operative element.

50. A device as claimed in claim 48 wherein the housing defines an inner lumen, and the two support blocks are at least partially located within the inner lumen in a snug fit.

51. A device as claimed in claim 50 wherein the two support blocks together have a combined cross-sectional area substantially equal to the cross sectional area of the inner lumen.

52. A device as claimed in claim 48 wherein the support block is substantially hemi-spherical in shape.

* * * * *